United States Patent [19]

Blackshear, Jr.

[11] 4,364,747
[45] Dec. 21, 1982

[54] SYSTEM FOR REGENERATIVE THERMALLY REVERSED ADSORPTION

[75] Inventor: Perry L. Blackshear, Jr., Mahtomedi, Minn.

[73] Assignee: The Regents of the University of Minnesota, Minneapolis, Minn.

[21] Appl. No.: 828,924

[22] Filed: Aug. 29, 1977

[51] Int. Cl.$^3$ .......................................... B01D 53/04
[52] U.S. Cl. ...................................... 55/25; 55/62; 55/74; 55/179; 55/208; 210/321.2
[58] Field of Search .................. 60/282, 308, 312; 55/202, 208, 209, 210, 179, 180, 33, 62, 74, 75, 390, 25; 210/24, 30, 34, 35, 177, 321 B

[56] References Cited

U.S. PATENT DOCUMENTS

| | | | |
|---|---|---|---|
| 3,085,379 | 4/1963 | Kiyonaga et al. | 55/62 X |
| 3,228,876 | 1/1966 | Mahon | 210/22 |
| 3,296,773 | 1/1967 | Hemstreet | 55/208 |
| 3,369,874 | 2/1968 | Wilhelm | 210/24 X |
| 3,583,907 | 6/1971 | Borsonyi | 210/22 |
| 3,734,293 | 5/1973 | Biskis | 55/208 X |
| 3,742,946 | 7/1973 | Grossman | 210/22 A |

OTHER PUBLICATIONS

Sparks et al., "Adsorption of Nitrogeneous Metabolite from Artificial Kidney Dialyzing Fluid", Chem. Eng. Prog. Symp. No. 66, vol. 62, pp. 2-10.
Reyerson et al., "Sorption and Magnetic . . . Temperatures", J. of P. Chem. 63, p. 1622, 1959.
Giordano et al., "Annual Report on Oxystarch in Uremia" 1-19-75-7-18-76; p. 40.
Wilhelm et al., Ind. Eng. Chem. Fund. vol. 7, p. 337, 1968.
Popovich et al., "Physiological Transport Parameters . . . Hemodialysis," pp. 126-128b, 1976.
Riaz, "Transient Analysis of Packed-Bed Thermal Storage Systems", 7-7-77.
Rhee et al., Chem. Eng. J. 3/72, pp. 121-135.

*Primary Examiner*—Ferris H. Lander
*Attorney, Agent, or Firm*—Burd, Bartz & Gutenkauf

[57] ABSTRACT

A system for the adsorption of a substance from a warm fluid containing the same. An initially relatively cool bed of adsorbent is fed with a relatively warm fluid containing an adsorbate. A sharp thermal wave is generated as the warm fluid enters the cool bed. A high pulse in concentration of the adsorbate develops ahead of the thermal front if the bed properties are appropriate. The concentration of adsorbate immediately ahead of the wave is related to adsorbate concentration in the inlet stream, the shape of the adsorption isotherms, the effective heat capacities and the original and final bed temperatures, bed design, thermal conductivities and dispersivities. There is a sharp drop in concentration at the forward edge of the concentration pulse. This pulse in adsorbate concentration is harvested by aspirating fluid from the bed at the time the pulse arrives at the end of the bed. For some purposes a total cycle of discharge and recharge of the bed is desirable. Following the discharge of the high concentration pulse from the bed, the bed is seen to be filled with fluid at the inlet concentration and temperature in approximate equilibrium with the solid. When the flow of fluid, free of the removed adsorbate, is passed through the bed at the cool temperature, a concentration wave will precede the thermal wave toward the original bed inlet. All the fluid that leaves the bed before the concentration wave reaches the inlet is desirably recycled. Provisions for the mass flow imbalance are proposed. The general requirements for this recycling process are described. The system is useful, for example, for concentrating urea in an artificial kidney, for concentrating NO in engines and power plants for oxidation to $NO_2$ and subsequent capture, for concentrating $SO_2$ in exhaust gases of systems using sulfur-bearing fuels, for concentrating organic impurities for removal from water, for concentrating alcohol, and the like.

8 Claims, 12 Drawing Figures

SYSTEM FOR REGENERATIVE THERMALLY REVERSED ADSORPTION

BACKGROUND OF THE INVENTION

1. Field of the Invention

This invention relates to a system for the concentration of adsorbates by thermally reversed adsorption of adsorbates of various kinds, solutes and gases, from solvents or other fluid carriers. A relatively warm fluid containing the adsorbate is fed to an initially relatively cooler adsorbent bed. As the warmer fluid moves through the bed a high pulse in concentration of the adsorbate develops immediately ahead of the thermal front, if the bed properties are appropriate. To insure the desired properties of the bed, the thermal (or adsorptive) properties of the bed (in respect to the adsorbate of interest) are modified such that at a mean temperature the solute adsorbed per unit volume in the solid, n, divided by that in the fluid, c, (for c→0) is approximately equal to the volume heat capacity of the solid $\rho_s c_{ps}$ divided by that of the fluid $\rho c_p$. [Note: when heats of adsorption contribute materially they will modify the $$\frac{\rho_s c_{ps}}{\rho c_p}$$

ratio]. The ratio of these ratios $$\frac{n}{c} \quad \frac{\rho c_p}{\rho_s c_{ps}}$$

is a function of concentration c and temperature. The packed bed is chosen such that $$\frac{n}{c} \quad \frac{\rho c_p}{\rho_s c_{ps}} > 1$$

at the initial bed temperature (as c→0) and becomes $$\frac{n}{c} \quad \frac{\rho c_p}{\rho_s c_{ps}} \leq 1$$

at the elevated concentration desired. The fluid is introduced at a temperature such that $$\frac{n}{c} \quad \frac{\rho c_p}{\rho_s c_{ps}} < 1$$

at the initial concentration.

A sharp thermal wave is generated as the hot fluid enters the cool bed. The concentration in the pulse of adsorbate immediately ahead of the wave, $c_2$ (at T2) is related to solute concentration in the inlet stream, $c_i$, by:

$$\frac{c_2}{c_i} = \frac{1 - \left(\frac{n}{c} \cdot \frac{\rho c_p}{\rho_s c_{ps}}\right)_i}{1 - \left(\frac{n}{c} \cdot \frac{\rho c_p}{\rho_s c_{ps}}\right)_2}$$

Note that $$\left(\frac{n}{c}\right)_2$$

is evaluated at the lower temperature and the concentration $c_2$. The width of the pulse is proportional to the mass that has passed though the thermal front. There is a sharp drop in concentration at the forward edge of this concentration pulse. This pulse in solute concentration is harvested by aspirating fluid from the bed at the time the pulse arrives at the end of the bed.

Following the discharge of the high concentration pulse from the bed, the bed is found to be filled with fluid at the inlet concentration and temperature in approximate equilibrium with the solid. When the flow of fluid, free of the removed adsorbate, is passed back through the bed at the cool temperature, a concentration wave will precede the thermal wave toward the original bed inlet, if the appropriate value of n/c and $$\frac{\rho c}{\rho c_s}$$

have been selected. All the solution that leaves the bed before the concentration wave reaches the inlet is recycled. When the thermal wave reaches the original inlet, the bed has been regeneratively recharged in respect to adsorbate as well as temperature with the exception of the imbalance caused by the harvested fluid concentrate. Provisions for this mass flow and hence heat flow imbalance are proposed. The general requirements for the thermal and physical properties and operating conditions that permit this recycling process to be accomplished are described.

2. The Prior Art

Activated charcoal is used in many clean-up processes and has been applied at low temperature in the removal of urea and other unwanted solutes from the dialysate of an artificial kidney (1) (FIG. 5 of Giordano et al, page 40, "Annual Report on Oxystarch in Uremia" to the National Institute of Arthritis and Metabolic Diseases, Artificial Kidney-Chronic Uremia Program, Jan. 19, 1975, to July 18, 1976.) The cyclical use of two temperatures to achieve purification or concentration has been published by Wilhelm and his colleagues (2) (Ind. Eng. Chem. Fundamentals, Vol. 7, p. 337, 1968 and U.S. Pat. No. 3,369,874.)

The present invention is more nearly related to some aspects of high temperature chromatography. (3) (Rhee et al., "An Analysis of an Adiabatic Adsorption Column Part IV: Adsorption in the High Temperature Range." The Chemical Engineering Journal, Vol. 3, pp. 121-135, 1972.) In example 5 of reference (3) the initially cool packed bed was fed wlith hot $N_2$ carrying benzene. It was shown that under certain conditions:

a. A pulse of benzene could be generated having a higher concentration than the inlet concentration and would move with the thermal wave velocity.

b. The concentration behind the pulse returned to the inlet concentration.

The example was constructed for an adiabatic system in which a solute adsorbed on the solid according to Langmuir adsorption. The example conditions were selected such that adsorption reversal occurred: the bed was initially cool such than n/c exceeded $(\rho c_p)_s/(\rho c_p)$ and was fed with a hot fluid such that n/c was less than $(\rho c_p)_s/(\rho c_p)$. The present invention pertains to those beds that exploit the concentrating potential of the adsorption reversal condition either through the selection of the temperature range or the thermal modification of the bed to bring $$\frac{n}{c} \quad \frac{\rho c_p}{\rho_s c_{ps}}$$

close to unity.

In the experiments of Popovich et al. (4) ("Physiological Transport Parameters in Patients in Peritoneal and Hemodialysis," Contract NO1-AM-3-2205. Proceedings of the Ninth Annual Contractors' Conference of the Artificial Kidney Program of the National Institute of Arthritis, Metabolism, and Digestive Diseases, pp. 126–128b, 1976.) it was shown that if 20 liters per day of dialysate were equilibrated with the blood through peritoneal lavage throughout a virtually 24 hour period (with a net water removal rate of approximately two liters per day), the uremic patient could be maintained indefinitely. It was felt in these preliminary considerations that an adsorbent that could concentrate and remove the unwanted solutes from the fluid draining from the peritoneal cavity could reduce the amount of fluid required, and thus the overall mass could be carried by the patient. Preliminary calculations based on thermal energy storage experiments and, in particular, a recent analytical paper by Riaz (5) ("Transient Analysis of Packed-Bed Thermal Storage Systems." presented at the International Solar Energy Society annual meeting, Orlando, Fla., June 7, 1977.) lead to the realization that the propagation velocity of the thermal wave could be modified such that adsorption reversal could occur for a wide range of adsorbates and adsorbents employing the data of Giordano et al. (1) and (6) (Sparks et al, "Adsorption of Nitrogenous Waste Metabolites from Artificial Kidney Dialyzing Fluid." Chemical Engineering in Medicine, Chemical Engineering Progress Symposium Series, No. 66, Vol. 62, pp. 2–10.) Preliminary calculations showed that a system to concentrate urea by adsorption reversal could be accomplished by adding non-adsorbing thermal sinks to the bed.

Giordano et al. (1) and Sparks et al. (6) have shown that adsorption of urea on charcoal is reversible (as are most physical adsorptions) and the bed can be washed for reuse by flushing with a clean solvent. Experience with storage heat exchangers has shown that they can be restored to the initial temperature through purging.

The need to restore the bed to its initial conditions of concentration and temperature with a minimum of added fluid in the artificial kidney problem led to the design of a doubly regenerative system that concentrates a solute, then cools and cleans the bed for reuse without the need for any extra purging fluid. This system, with respect to urea, acts as an artificial loop of Henle.

In the treatment of uremic patients ultrafiltrate purification and reintroduction is not practiced at present. Current research that appears in the literature includes:

1. The use of charcoal column at low temperatures to adsorb urea, creatinine, and presumably other unwanted solutes at 0° C. from precooled dialysate (Giordano et al.) (1). Here the charcoal can be regenerated by purging with warm water and reused. The important contribution of Giordano et al is the demonstration that the adsorption isotherms for urea and creatinine on a representative charcoal are significantly different at 37° C. and 0° C.

2. A technology that could be employed but has not yet been employed for this purpose is parametric pumping (Wilhelm et al.) (2) wherein solute concentrations can be raised on one side of a column, reduced on the other side by the synchronous alternations of flow direction and bed temperature. The similarity rests in reliance on the change in adsorptivity with temperature.

3. Rhee et al. (3) described the fundamental phenomena that are responsible for the effect exploited in the current design. The system described by Rhee et al is a gas-solid system where adsorption reversal is easily attained. The possibility of thermally modifying the bed material to insure adsorption reversal at the desired temperature range has not been discussed so far as is known.

4.

Popovich (4) has employed peritoneal lavage virtually around the clock to establish the potential efficacy of continuous solute removal from dialysate in maintaining a uremic patient.

SUMMARY OF THE INVENTION

Broadly stated, the invention is directed to that class of adsorbate concentrators that develops a peak of concentration immediately ahead of a thermal front when a relatively warm adsorbate containing fluid is introduced into an initially relatively cool adsorbing column. The peak is achieved by either operating the bed at conditions where adsorption reversal occurs in the material at hand or modifying the bed composition such that adsorption reversal occurs over the operating temperature and composition range. For example, in the case of the use of adsorption reversal solute extraction in the artificial kidney, urea flowing through a character bed at the temperature at which the artificial kidney is constrained to operate would not permit reversal to occur in the beds studied by Giordano (1) at the imposed conditions. However, adding non-adsorptive material with a high volumetric heat capacity makes it possible to bring the bed to adsorptive and thermal conditions where adsorptivity reversal can occur at the desired temperature and composition ranges. Then the device proposed would produce a high concentration of urea immediately ahead of the advancing temperature front. Thus, the invention includes all those adsorption systems that are operated at conditions which permit adsorption reversal to occur across the thermal front.

The invention also includes the mode of operation of the fundamental process in a way to optimize its energy and solute conservation in a regenerative cycle. It was designed particularly with the artificial kidney in mind, but has utility in diverse other purification processes. The essential features of this doubly regenerative system are: (1) The heat flow in the two directions is balanced, despite the fact that there is a net harvest of fluid; thus regenerative heat exchange is accomplished and energy conserved. (2) This thermal regeneration and the restoration of the bed to its original "clean" condition is accomplished by requiring some of the fluid particles to pass through the bed several times.

The invention also includes a specification of the bed physical and thermal properties as they influence axial dispersion of heat and adsorbate. Selection of particle (or tube) size and shape, adsorbent thickness and effective adsorbate diffusion coefficients, as well as dispersion by non-uniform flow, are selected to maintain axial dispersion of the concentration pulse within design limits.

BRIEF DESCRIPTION OF THE DRAWINGS

The invention is illustrated in the accompanying drawings in which corresponding parts are identified by the same numerals and in which.

DESCRIPTION OF THE PREFERRED EMBODIMENTS

Figures 1, 1C:
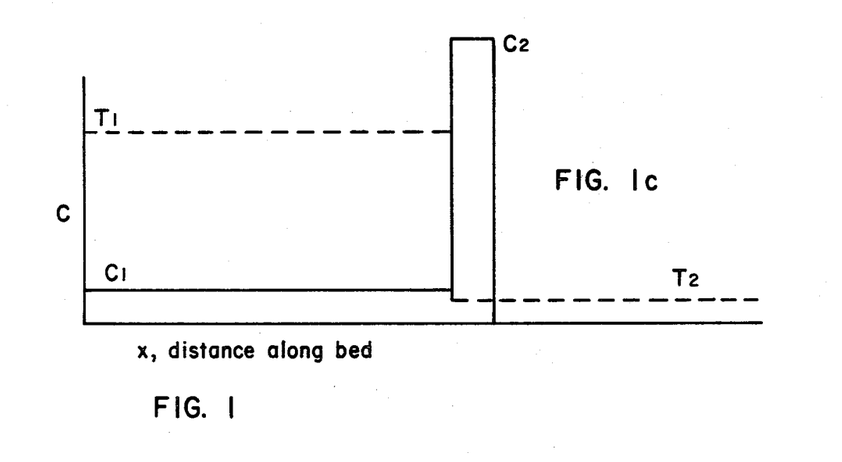
FIG. 1c is a graphic representation of the qualitative behavior of the thermal and composition fronts.

The conditions under which an adsorbate concentrator may be operated so as to develop a peak of concentration immediately ahead of a thermal front when a relatively warm adsorbate containing fluid is introduced into an initially relatively cool adsorbing bed can be briefly stated as follows: A bed is initially at a temperature at which the quantity $$\frac{n}{c} \frac{\rho c_p}{\rho_s c_{ps}}$$

is greater than 1 (as c approaches zero) and becomes less than unity at approximately the elevated concentration desired. The fluid containing the adsorbate which is to be concentrated is introduced at a temperature such that $$\frac{n}{c} \frac{\rho c_p}{\rho_s c_{ps}}$$

is less than unity at the initial concentrations. When the temperatures are prescribed by the constraints of the device (as in the case of the artificial kidney), the bed is modified by adding thermal sinks such that the desired behavior of the quantity $$\frac{n}{c} \frac{\rho c_p}{\rho_s c_{ps}}$$

can be achieved. The pertinent relationships are shown in FIG. 1.

Figure 1A:
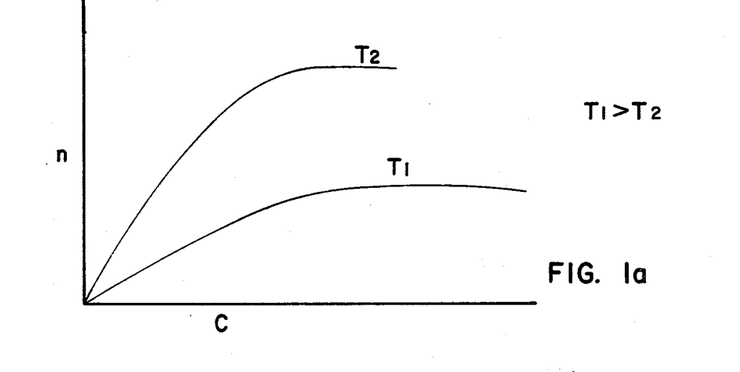
FIG. 1a is a graphic representation of sample isotherms at two temperatures from which concentration of solute ahead of the thermal wave can be determined.

FIG. 1a shows sample isotherms at two temperatures, $T_1$ and $T_2$. The process is possible when n/c at $T_2$ is greater than $$\frac{\rho_s c_{ps}}{\rho c_p}.$$

When this condition is satisfied non-adsorbing heat sinks are added to the bed such that n/c is less than $$\frac{\rho_s c_{ps}}{\rho c_p}$$

at $T_1$ and greater than $$\frac{\rho_s c_{ps}}{\rho c_p}$$

at $T_2$. All values of n/c are evaluated at the inlet concentration. The conditions that result from mass conservation across the thermal front yield:

$$c_1\left(1 - \left(\frac{n}{c} \frac{\rho c_p}{\rho_s c_{ps}}\right)_1\right) = c_2\left(1 - \left(\frac{n}{c} \frac{\rho c_p}{\rho_s c_{ps}}\right)_2\right)$$

Figure 1B:
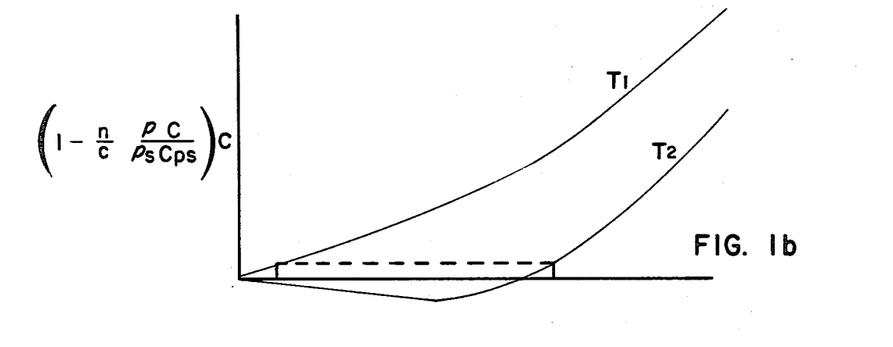
FIG. 1b is a graphic representation of the pertinent relationships between adsorptivity, concentration and temperature that determine the height of the concentration pulse.

$c_2$ can be solved graphically in FIG. 1b.

The qualitative behavior of the thermal and composition fronts are shown in FIG. 1c.

There are other minor variations of this general requirement that will insure sharp boundaries in concentration. These have to do with bed design and operating conditions to insure a sharp temperature front: particle size selection to produce the desired rapidity of mass exchange between fluid and particle and other factors which lead to the production of a sharp front. For example, the addition of the non-adsorbing thermal sinks should be accomplished with the porous material in a thin shell over a heat adsorbing matrix. When these are sufficiently successful that equilibrium conditions prevail, the concentration ratio across the thermal front becomes:

$$c_2/c_1 = \frac{1 - \left(\frac{n}{c} \frac{\rho c_p}{\rho c_{ps}}\right)_1}{1 - \left(\frac{n}{c} \frac{\rho c_p}{\rho c_{ps}}\right)_2}$$

When energy and fluid economy is not of moment and the concentration of a particular solute is desired, the system can be recycled in a number of ways as a batch processor.

The mode of operation of the fundamental process in a way to optimize its energy and solute conservation in a regenerative cycle, designed particularly with the artificial kidney in mind, is demonstrated by reference to FIGS. 2 through 9. The system, in the form of a wearable artificial kidney, indicated generally at 10, includes an array of long narrow packed beds contained within tubes 11 arranged about a cylinder adapted to rotate about a central axis, driven by motor means (not shown). The ends of tubes 11 are supported by smooth polished planar left and right end plates 12 and 13, respectively, which in engagement with similar smooth polished planar surfaces on left and right end manifolds 14 and 15, respectively, form rotary seals. Manifold 14 includes a plurality of isolated passages 16-20 arrayed in circular configuration such that the passages communicate with the ends of tubes 11. Manifold 15 has a plurality of similarly arrayed passages 21-26 communicating with the opposite ends of tubes 11. A tube 27 transmits fluid from a patient to manifold passage 16. A similar tube 28 transmits purified fluid from manifold passage 19 back to the patient. Manifold passages 17 and 18 are interconnected by tube 29. Left end manifold passage 20 is interconnected with right end manifold passage 26 by tube 30. Tube 31 connected to right end manifold passage 23 serves as a waste discharge. Manifold passages 21 and 24 are interconnected by tube 32. Manifold passages 22 and 25 are interconnected by tube 33. Tube 30 is cooled by passage through appropriate heat exchange means 34, such as an ice chamber or in exchange with the voided fluid.

Figure 7:
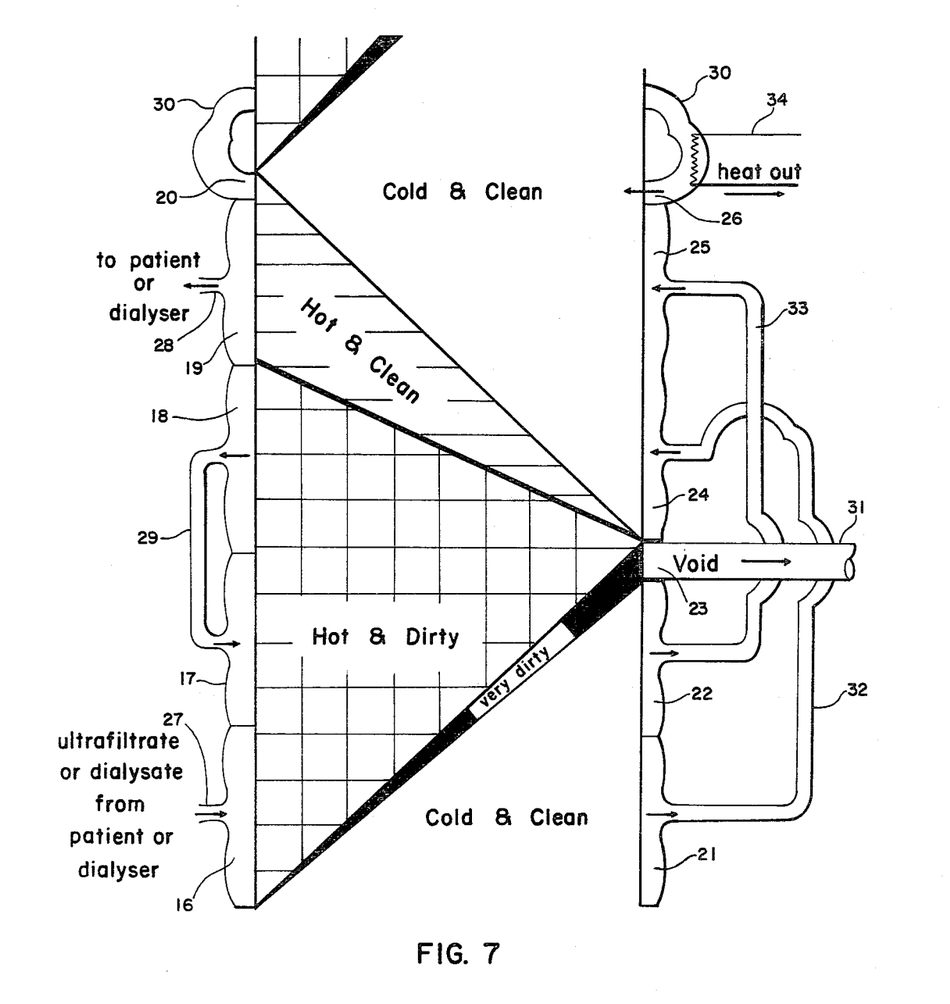
FIG. 7 is a schematic representation illustrating one cycle of operation of the regenerative concentrator.
Figure 8:
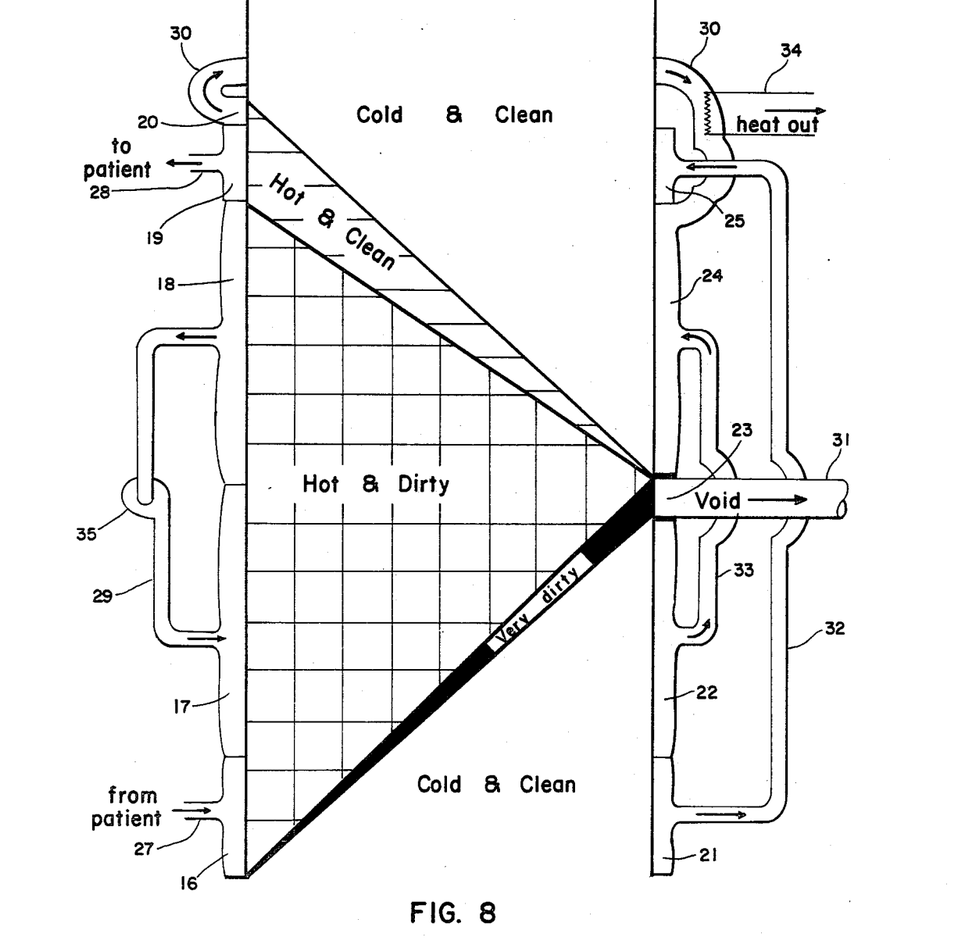
FIG. 8 is a similar schematic representation illustrating a cycle of operation when operating conditions require a mismatch in the inlet flow and that in the recycling loop.

FIG. 7 shows in diagrammatic form the operation of the device through one cycle of operation. The diagram of FIG. 7 represents the beds and manifolds unwound from their cylindrical form to planar form with the manifolds appearing as the vertical axis with distance along the packed beds being measured along the horizontal axis. The distance from bottom to top of the beds represents increasing time (one rotation) and can be pictured as the sequence of events an observer would witness as the tube he rides on passes the several pairs of manifolds. The fluid flow paths and conditions of the fluid are shown. The waste concentrated ahead of the thermal front is flushed from the system and discharged through tube 31. As seen, thermal balance is maintained by recycling a small loop of clean fluid in passage 30 through a heat exchanger 34. The patient can conveniently carry a small ice pack for achieving this cooling.

The essential features of the doubly regenerative system are demonstrated showing that the heat flow in two directions is balanced despite the fact that there is a net harvest of fluid and the thermal regeneration and restoration of the bed to its original condition is accomplished by passage of some of the fluid particles through the bed four complete times.

In the diagram of FIG. 7, the manifolds are arrayed in such a manner that the flow can be maintained by a single pump. This convenience is often available. However, if the operating conditions require a mismatch in the inlet flow and that in the recycling loop, the design shown in FIG. 8 can be employed in which an added pump 35, shown schematically, may be used. The system may be used for purifying a dialysate or ultrafiltrate in the use of either dialyzers or peritoneal dialysis to maintain the chronic uremic patient.

The regeneration of dialysate and ultrafiltrate by charcoal has been successfully accomplished by a number of investigators, but the one aspect of the system not yet accomplished by charcoal or any other sorbent of convenient volume is the removal of urea. A bed designed to remove urea by the process proposed can be accomplished by adding non-adsorbing, heat adsorbing mass. For example, stainless steel particles, such that the quantity of $$\frac{n}{c} \quad \frac{\rho c_p}{\rho_s c_{ps}}$$

inferred from the value reported by Giordano (1) of something greater than unity can be reduced to something less than unity at $T_1$ while remaining greater than unity at $T_2$ (both for $c \rightarrow 0$). Then the behavior of FIG. 1a can be achieved.

Figures 2, 10:
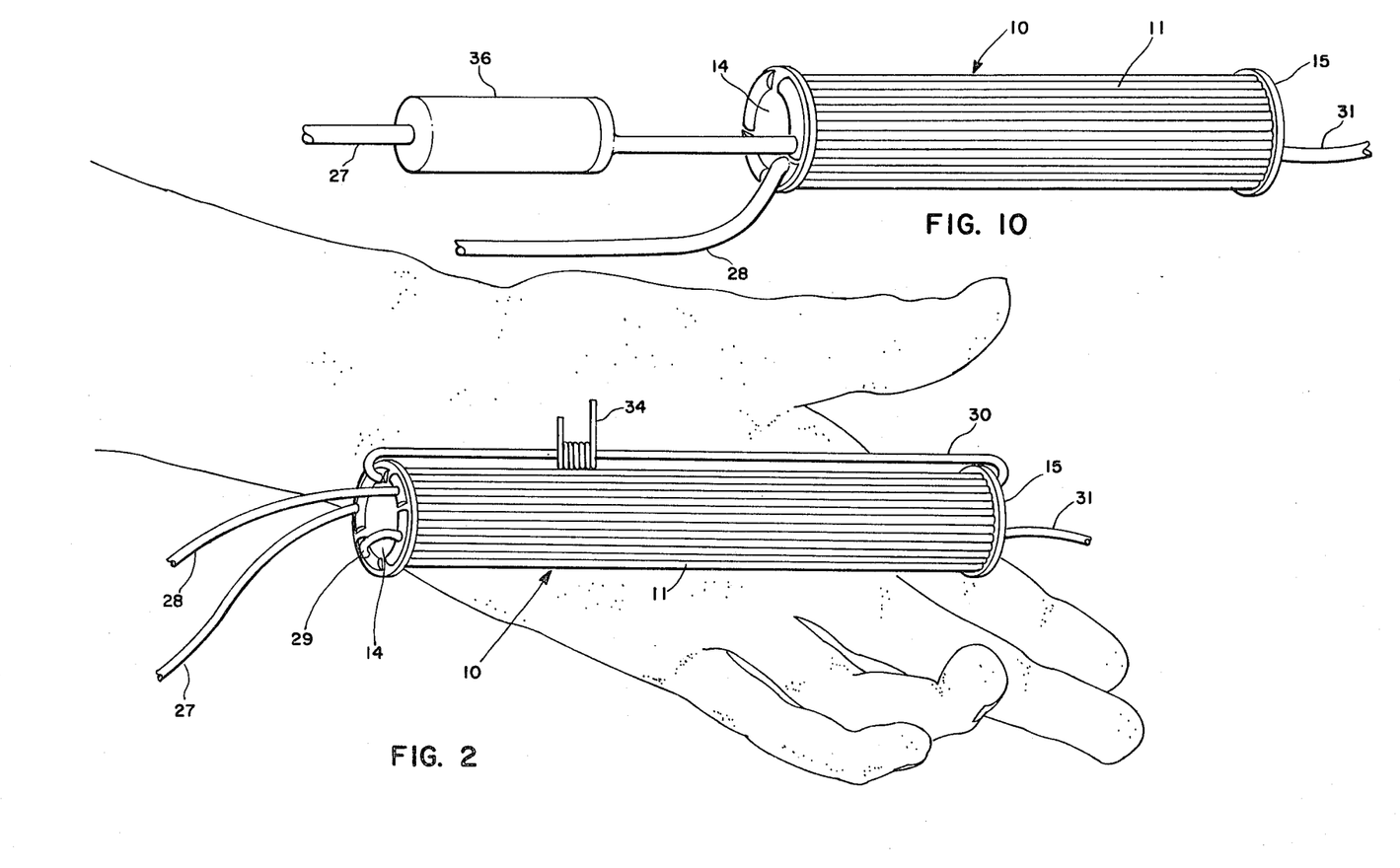
FIG. 2 is a perspective view of a regenerative thermally reversed adsorption concentrator which may be used as part of a wearable artificial kidney.
FIG. 10 is a schematic representation of a system for the elimination of non-ionic species in ultrafiltrate or dialysate.
Figure 3:
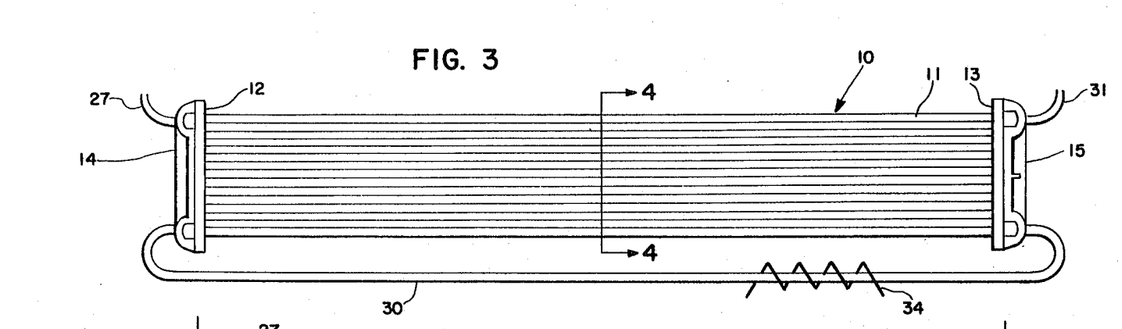
FIG. 3 is a schematic representation thereof.
Figure 4:
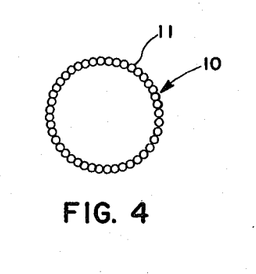
FIG. 4 is a section on the line 4—4 of FIG. 3.
Figure 5:
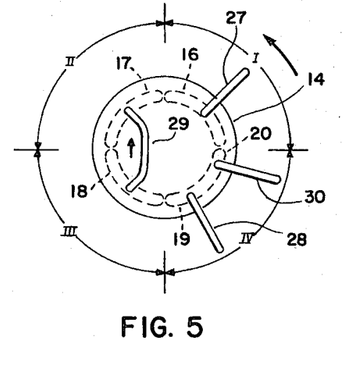
FIG. 5 is a left end view of the concentrator of FIG. 3.
Figure 6:
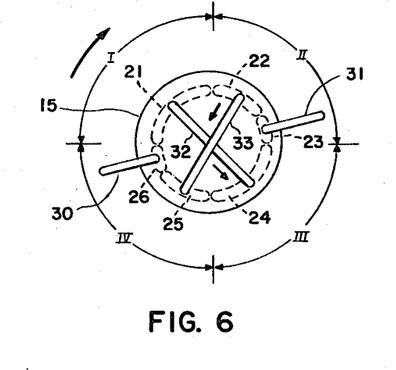
FIG. 6 is a right end view thereof.
Figure 9:
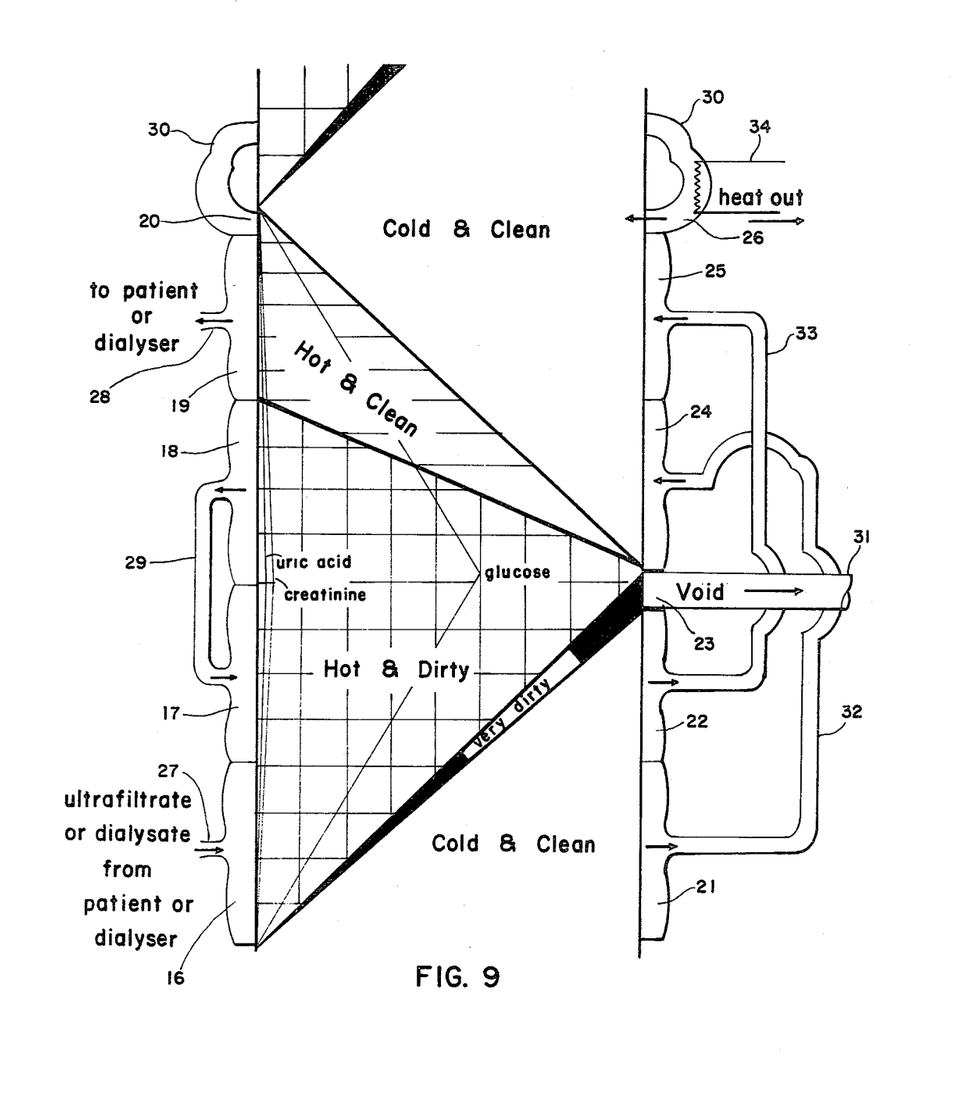
FIG. 9 is a similar representation showing the behavior effect of other solutes in a system designed for urea removal in an artificial kidney.

It is of interest to see how other solutes would behave in a system designed for urea removal. FIG. 9 shows a plot of the position of creatinine, uric acid, and glucose fronts that would appear in an adsorption reversal solute extractor designed for urea. It can be seen that the patient would get back virtually all uric acid and glucose that was introduced. The design proposed is shown in FIG. 10. It consists of a stationary charcoal cartridge 36 operated at 37° C. It is sufficiently short so that a creatinine front would just barely cross it during the course of the period of purification. Under those circumstances the uric acid and all other strongly adsorbed solutes would be captured by the charcoal bed. Glucose and urea would have passage times that are respectively 50 and 300 times shorter and therefore only two percent of the glucose is retained in the first bed and one percent of the urea. Since glucose is not retained in the regenerative thermally reversed adsorption column, it will be returned to the patient. Thus, by combining an isothermal adsorber designed for creatinine but not overdesigned for creatinine, it is possible to combine a conventional adsorber with the thermally modulated process to complete the removal of both strongly and weakly bound solutes without removing the glucose.

The system of the invention is adapted to the removal of sulphur dioxide from the exhaust of a coal burning power plant or the removal of organic impurities in a municipal water system. Once again the doubly regenerative capability of the adsorption reversal solute extraction system is desirable; the concentrated $SO_2$ stream produced by the RETRAC (Regenerative Thermally Reversed Adsorbate Concentrator) can be cleaned in a limestone scrubber at a fraction of the present cost. An estimate of the sizes of regenerative charcoal beds that would be required to capture and concentrate the $SO_2$ in this form suggests that 10 beds, 10 meters in diameter, could adequately process the exhaust of a 1000 mw coal burning plant.

In cleaning the organic impurities from municipal water supplies, European communities employ charcoal filters which require a considerable volume of the available water to clean the charcoal for repeated use. By taking advantage of waste heat from power plants, the RETRAC can be used to eliminate particular pollutants with a minimum of water for regenerating the charcoal.

In these two applications, single solutes are to be removed. Therefore, carefully designed single beds could produce a narrow band at high concentration.

The system is also adapted to the concentration of alcohol-water solution. Here the issue is not so much to purify the water as to concentrate the alcohol with a minimum of energy expenditure. The thermally regenerative capability of adsorption reversal solute extraction makes possible the concentration of alcohol at an energy cost about 15 percent of the energy required to bring the original solution from the low temperature employed to the elevated temperature employed. Thus, energy inefficiencies can be reduced.

A still further application of the invention is one in which the goal is to produce a retention of a relatively non-reactive solute in a flowing stream long enough for it to react with another reagent. For example, nitric oxide is notoriously slow to react or adsorb with virtually anything. However, an inspection of experimental work done at the University of Minnesota by Reyerson et al. (8) ("Sorption and Magnetic Susceptibility Studies on Nitric Oxide-Silica Gel Systems at a Number of Temperatures.", Journal of Physical Chemistry, 63, p. 1622, 1959) has shown that NO is sufficiently adsorptive on silica gel that $$\frac{n}{c} \frac{\rho c_p}{\rho_s c_{ps}}$$

can be brought close to unity. The high build-ups of NO in a silica gel bed are feasible, and the retention times, therefore, can be made proportional to the thermal wave transit time in the bed. Thus, instead of a fraction of a second for the NO to be held, it can be held for tens of minutes. The $NO_2$ resulting from the oxidized NO retained in the bed now is more strongly adsorbed by the silica gel or its analogue and is therefore retained even for longer periods by the packed bed. In the prior art, efforts to find adsorbers had been rejected simply because no adsorber has the capability to adsorb significant quantities of NO. With the proposed system, adsorptivity reversal with temperature makes it possible to retain NO with adsorbents presently available. Adsorbers like silica gel can be used to retain the NO long enough for it to oxidize more easily collectable $NO_2$. In this latter application, it is conceivable that the thermal energy stored in the silica gel column would also be harvested at the end of the engine operation period and the recycling process would be performed in a time-varying application of the invention rather than a steady state.

In the design of the artificial kidney application of the adsorption reversal concentrator when actual data from Giordano (1) are used to construct a figure similar to 1$b$ it is found that urea entering at 60 mg/100 ml produces a concentration pulse height of 3700 mg/100 ml. Because the system requires elimination of 10 percent of the entering water only a 10 fold concentration is required. Thus, the specification for minimizing dispersion can be relaxed to give dispersion=0.1L where L is the length of the concentrator. Table I gives the results of this design specification.

TABLE I

Tube Design

Design Requirements ot process 20 liters of ultrafiltrate per day

Column is packed tubes, diameter $d_p$, length L (m)
Set dispersity, Ea, = thermal diffusivity, $\alpha$(m$^2$/s)

$$Ea = 10^{-6} m^2/s = \frac{d_p^2 U}{200 \cdot 10^9 \, m^2/s}, \text{ U is mean velocity}$$

Set dispersion = $\Delta x = \sqrt{4\pi Ea \frac{L}{U}} = 0.1 L$

Pressure drop $\Delta P =$

TABLE I-continued

Tube Design $$32 \frac{\mu UL}{d_p^2} = \frac{4 \cdot 10^{-5}}{d_p^2} \, N/m^2 < 2 \cdot 10^4 \, N/m^2$$

Specific Design Meeting Requirements $\frac{d_p}{L} = 3.6 \cdot 10^{-4}$ if L = 0.15 m, $d_p = 5.4 \cdot 10^{-5}$ m $\Delta P = 1.37 \cdot 10^4 \, N/m^2$ U = 8.3 $\cdot 10^{-3}$ m/s $\frac{\pi d_p^2}{4} = 0.29 \cdot 10^{-4}$ m$^2$/number of tubes Total flow area for regenerator is 1.16 $\cdot 10^{-4}$ m$^2$ It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A regenerative thermally reversible system for concentrating an adsorbate by reversing the relative adsorptivity of the adsorbate versus heat, said system comprising:

(A) providing an initially relatively cool adsorbent bed of a material capable of developing a peak of concentration of an adsorbate immediately ahead of a thermal front, said bed being composed of a highly adsorptive material in proximity to a non-adsorptive material having an effectively high volumetric heat capacity, (B) passing a relatively warmer adsorbate-containing fluid through said bed to create a thermal front therein, (C) first separating the resulting pulse of fluid freed from its contained adsorbate, (D) then separating the resulting pulse of concentrated adsorbate, both at the downstream end of the bed.

2. A system according to claim 1 wherein the adsorptivity of the warmed bed is thermally regenerated by cooling.

3. A regenerative system according to claim 2 wherein the bed is cooled and purged of adsorbate by recycling at least part of the fluid freed from its contained adsorbate.

4. A system according to claim 3 for regenerative operation in which at least one stationary bed can be used with appropriate storage and valving to accomplish the purposes of the regenerative operation of the thermal adsorptivity reversal concentrator.

5. A system according to claim 1 wherein said adsorptive material is disposed in a thin shell over a heat adsorbing matrix.

6. A system according to claim 1 wherein:
   (A) the adsorbent bed is chosen such that $$\frac{n}{c} \frac{\rho c_p}{\rho_s c_{ps}}$$

is greater than 1 at the initial bed temperature, where:

n is the adsorbate adsorbed per unit volume in the solid, c is the concentration in the inlet fluid, $\rho c_p$ is the volume heat capacity of the fluid, and $\rho_s c_{ps}$ is the volume heat capacity of the solid, (B) the fluid is introduced at a temperature such that $$\frac{n}{c} \frac{\rho c_p}{\rho_s c_{ps}}$$

is less than 1 at the initial concentration, and (C)

$$\frac{n}{c} \frac{\rho c_p}{\rho_s c_{ps}}$$

becomes equal to or less than 1 at the desired elevated concentration and at the initial bed temperature.

7. A system according to claim 6 wherein the bed after passage of a thermal front is returned to $$\frac{n}{c} \frac{\rho c_p}{\rho_s c_{ps}}$$

is greater than 1 by cooling.

8. A regenerative thermally reversible system for concentrating an adsorbate by reversing the relative adsorptivity of the adsorbate versus heat, said system comprising:

(A) providing an initially relatively cool adsorbent bed of a material capable of developing a peak of concentration of an adsorbate immediately ahead of a thermal front, (1) said adsorbent bed being disposed in a plurality of elongated tubes arrayed in cylindrical form, (2) means being provided to rotate said cylinder about a center longitudinal axis, (3) the ends of said tubes being supported in smooth polished planar end plates, (4) a manifold having a smooth polished planar surface being disposed at each end of said cylinder in engagement with the surface of one of said end plates, forming a rotary seal therewith, (5) each of said manifolds having a plurality of isolated passages therein, each in communication with the ends of some of said tubes, (6) a fluid inlet being provided to one of said manifold passages and a fluid outlet is provided from another of said manifold passages, (7) an adsorbate discharge being provided from still another of said manifold passages at the end of the cylinder opposite from the fluid inlet, (8) a fluid recycling duct being provided connecting one manifold passage at one end of the cylinder with a corresponding manifold passage at the opposite end of the cylinder, and (9) heat exchange means being provided in association with said recycling duct, (B) passing a relatively warmer adsorbate-containing fluid through said bed to create a thermal front therein, (C) first separating the resulting pulse of fluid freed from its contained adsorbate, (D) then separating the resulting pulse of concentrated adsorbate, both at the downstream end of the bed, and (E) cooling the bed and purging it of adsorbate by recycling at least part of the fluid freed from its contained adsorbate.

* * * * *

UNITED STATES PATENT AND TRADEMARK OFFICE
CERTIFICATE OF CORRECTION

PATENT NO. : 4,364,747
DATED      : December 21, 1982
INVENTOR(S): Perry L. Blackshear, Jr.

It is certified that error appears in the above-identified patent and that said Letters Patent is hereby corrected as shown below:

Column 4, lines 37 and 38, "character" should be --charcoal--.

Column 9, line 56, "ot" should be --to--.

Signed and Sealed this

Twelfth Day of April 1983

[SEAL]

Attest:

GERALD J. MOSSINGHOFF

Attesting Officer

Commissioner of Patents and Trademarks